United States Patent [19]
Rutten

[11] Patent Number: 6,076,019
[45] Date of Patent: Jun. 13, 2000

[54] FLEXIBLE AND ADJUSTABLE DDD LEAD

[75] Inventor: Jean J. G. Rutten, El Bocholtz, Netherlands

[73] Assignee: Medtronic, Inc., Minneapolis, Minn.

[21] Appl. No.: 09/132,000

[22] Filed: Aug. 10, 1998

[51] Int. Cl.[7] .................................................. A61N 1/04
[52] U.S. Cl. ........................................................ 607/123
[58] Field of Search .................................. 607/119, 122, 607/123, 125

[56] References Cited

U.S. PATENT DOCUMENTS

| | | | |
|---|---|---|---|
| 4,154,247 | 5/1979 | O'Neill. | |
| 4,401,126 | 8/1983 | Reenstierna | 178/784 |
| 5,405,374 | 4/1995 | Stein | 607/122 |
| 5,609,621 | 3/1997 | Bonner | 607/122 |
| 5,628,778 | 5/1997 | Kruse et al. | 607/123 |

OTHER PUBLICATIONS

Brownlee, Robert R. et al., "Toward Optimizing A Pre-shaped Catheter and System Parameters to Achieve Single Lead DDD Pacing," *PACE*, vol. 20, May 1997, Part I, pp. 1354–1358.

*Primary Examiner*—Scott M. Getzow
*Attorney, Agent, or Firm*—Thomas F. Woods; Michael J. Jaro; Harold Patton

[57] ABSTRACT

The present invention provides a cardiac pacing system with a DDD lead with pre-stressed curvilinear portions, the lead being able to adapt to heart movement and size so as to provide more stable positioning with respect to the atrium. The lead has at least three such pre-stressed curvilinear portions positioned to adapt to the patient's heart and to absorb movement due to contractions so as to maintain atrial electrodes in a stable position with respect to the atrial wall.

17 Claims, 4 Drawing Sheets

FLEXIBLE AND ADJUSTABLE DDD LEAD

FIELD OF THE INVENTION

The present invention relates to the field of body-implantable medical device systems, and in particular to a flexible and adjustable DDD lead.

BACKGROUND OF THE INVENTION

It has long been a desire and aim in the pacemaker art to provide a reliable single lead for use with a dual chamber pacing system. As is known, in the past a conventional dual chamber system typically has utilized two leads which interconnect the implanted pacemaker with the ventricle and atrium, respectively. Thus, in such a system a ventricular lead interconnects the pacemaker with the ventricle, delivering ventricular pace pulses to the ventricle and sensing ventricular conduction activity and returning such sensed signals to the pacemaker. A second, atrial lead is provided for performing the same functions with respect to the atrium. A long recognized disadvantage of this arrangement is the need to provide two leads, which adds to expense and increases reliability problems; and also takes significantly more physician time in placing the two leads at time of implantation.

The VDD or VDD(R) single pass lead provides a response to the two-lead problem, and has been in use for some time. In such a single lead construction, the distal tip has a fixation mechanism for fixing to the apex of the ventricle, while the lead is essentially "floating" or unattached in the atrium. The VDD lead is provided with one or two atrial electrodes, typically ring electrodes which are positioned in the atrium, for sensing P wave signals, thereby providing the ability to time out an AV delay and provide ventricular pace pulses which are synchronized to sensed atrial depolarizations. While some attempts have been made to pace from floating atrial electrodes, this has generally been ineffectual.

A further advance is what is known as the DDD lead, which has enhancements which aim to provide more stable contact with the atrial wall, so as to enable more reliable atrial pacing as well as reliable atrial sensing. The DDD lead typically includes features added to the lead portion to enable DDD operation, i.e., pacing and sensing in both chambers. The additional features are intended to maintain the atrial electrodes closer to the atrial wall when the distal tip is anchored to the ventricular apex. These features may include, for example, an atrial tine, or small extension from the lead body, which may be designed to provide better fixation against the atrial wall. The atrial tine may also be provided with a distal electrode, for making direct contact with the atrial wall. Other features which have been adapted to DDD-type leads include a variety of S-shaped leads and pre-shaped sections, for the purpose of providing more stable atrial positioning. See, for example, U.S. Pat. No. 5,628,778, Kruse; and U.S. Pat. No. 4,154,247, O'Neill; and "Towards Optimizing a Pre-Shaped Catheter and System Parameters to Achieve Single Lead DDD Pacing," PACE, Vol.20, May 1997, Part I.

There remains, however, a significant need to improve the ability of the DDD lead to accommodate different heart sizes, as well as heart movement due to ongoing contractions. Existing DDD leads are, to various degrees, not stable in the atrial area, do not adapt to heart size, and cannot move optimally with the heart during cardiac movement. There remains a significant need to adapt the DDD lead to heart movement and size, and to provide better anchoring with respect to the atrium.

SUMMARY OF THE INVENTION

In accordance with the above, the primary purpose of Applicant's claimed invention is to provide a DDD lead which is able to adapt to heart movement and size, and which provides better anchoring with respect to the atrium. The implantable DDD pacing lead of the present invention has a proximal end and a distal end, and a lead body extending therebetween. The lead body also has a ventricular section that extends to the distal end in order to position the lead within the patient's ventricle. The ventricular section has a first pre-stressed portion with a first radius of curvature. The lead body also has an intermediate section which is proximal to the ventricular section for positioning intermediate the patient's atrium and ventricle. The intermediate section has a second pre-stressed portion with a second radius of curvature. The lead body also has an atrial section which is proximal to the intermediate section for positioning in the patient's atrium. The atrial section has a third pre-stressed portion with a third radius of curvature. The ventricular, intermediate and atrial sections have sufficient flexibility so that the atrial section is maintained in a position proximal to the patient's atrial wall during heart contractions.

The DDD pacing lead further has at least one atrial electrode that is positioned within the atrial section and an atrial conductor within a lumen in the lead body which connects the proximal end of the lead to the atrial electrode. The DDD pacing lead also has at least one ventricular electrode that is positioned within the ventricular section at about the distal end and a ventricular conductor within a lumen in the lead body which connects the proximal end of the lead to the ventricular electrode.

The present invention further provides a system for pacing a patient's heart having a pacemaker and a DDD pacing lead as described above.

DESCRIPTION OF THE PREFERRED EMBODIMENTS

Applicant's invention provides an implantable DDD pacing lead for pacing a patient's heart. Standard straight leads are mostly manufactured in 3 or 4 sizes in order to properly fit most heart sizes. A major drawback to many pacing leads, however, is the failure to maintain proper positioning of the lead within the heart when the heart contracts. The present invention provides a flexible lead with an adjustable atrial-ventricular range so as to maintain positioning within the heart at the appropriate sites, e.g., maintain substantial contact with the electrodes. In addition, the flexibility of Applicant's leads may allow the user of the leads to stock fewer sizes of leads. The flexibility of Applicant's DDD pacing lead is accomplished by positioning of pre-stressed portions within the lead. Each pre-stressed portion has a particular radius of curvature, thus allowing for flexibility and adjustability of the atrial-ventricular range of the lead. The placement of pre-stressed portions in the lead provides the lead with an S-shape which provides the lead with sufficient flexibility.

Figure 1:
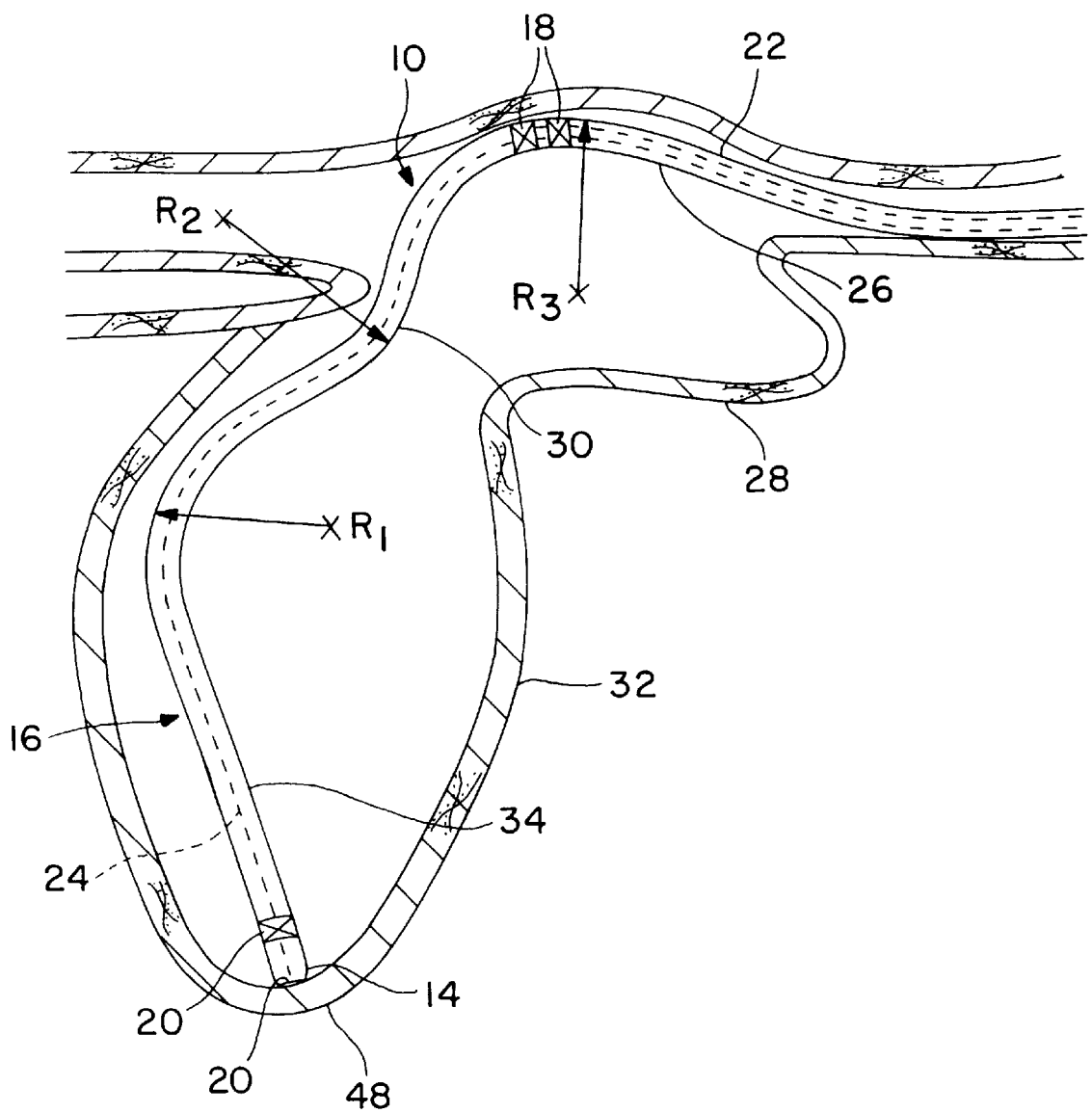
FIG. 1 is an illustrative representation of a preferred DDD pacing lead having respective first, second, and third radii of curvature and positioned within a patient's heart.
Figure 3:
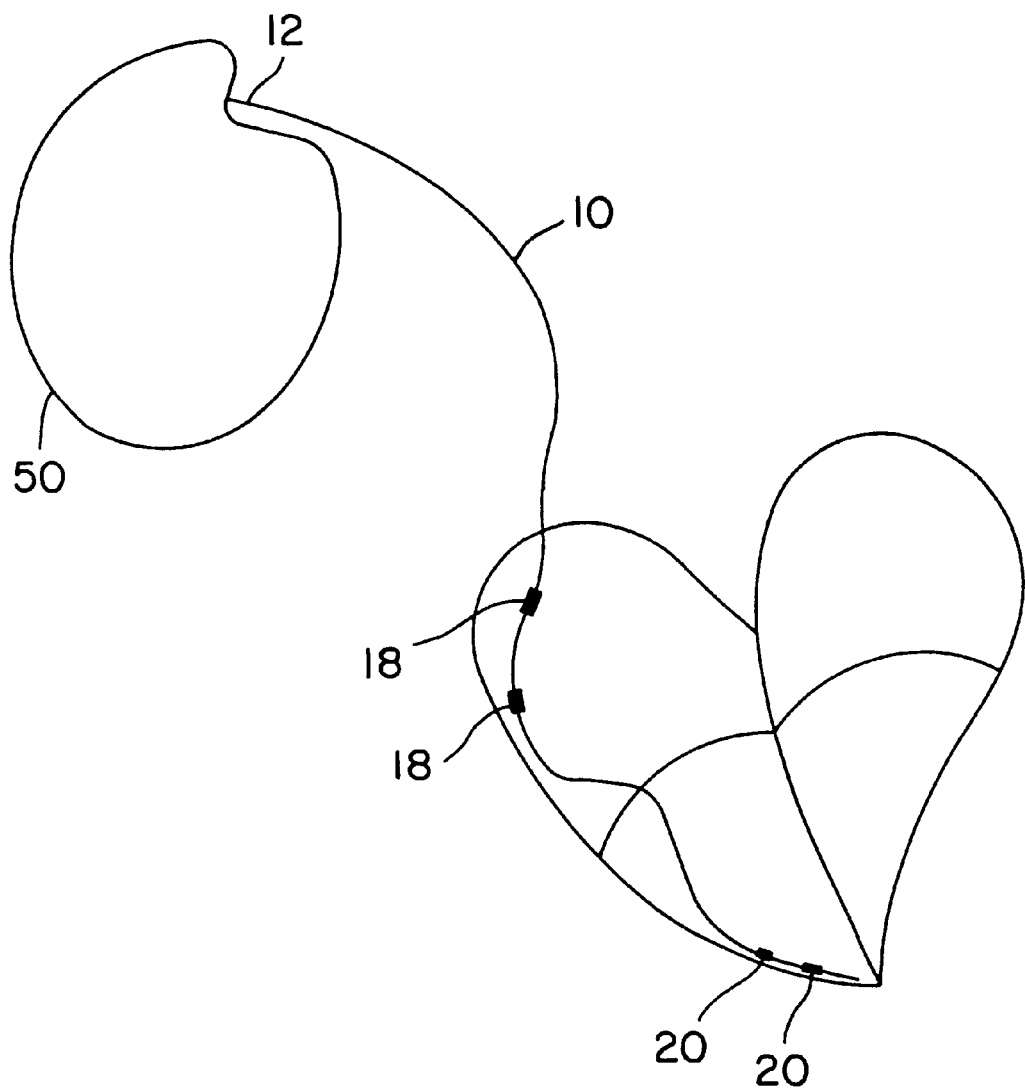
FIG. 3 is a diagrammatic sketch of a preferred system for pacing a patient's heart.

Referring now to FIG. 1, there is shown an illustrative embodiment of a preferred DDD pacing lead positioned within a patient's heart. The implantable pacing lead 10 for DDD pacing of a patient's heart has a proximal end 12 (as seen in FIG. 3) and a distal end 14. The proximal end is connectable to a pacemaker. The distal end is positioned in the apex 48 of the ventricle 32. In some embodiments of the invention, the distal end may also have a screw-in element which is screwed into the ventricular wall for providing additional anchoring and support for the lead. Screw-in elements are well known to those skilled in the art. A lead body 16 extends between the distal and proximal ends. The lead body is preferably made of non-conductive or insulative materials widely known to those skilled in the art of implantable leads. In addition, the lead body is preferably between about 1.0 and 4.0 mm in diameter, and more preferably between about 2.0 and 2.5 mm in diameter. The lead body is preferably made of silicone rubber or other equivalent, suitable material known to those skilled in the art.

The lead body has a ventricular section 34 which extends to the distal end of the lead for positioning in the patient's ventricle. The ventricular section begins at a point on the lead located from about 90 mm to about 150 mm from the distal end of the lead and extends to the distal end of the lead. The ventricular section has a first pre-stressed portion with a first radius of curvature $R_1$. Preferably, the first radius of curvature is between about 25 mm and 35 mm. The first pre-stressed portion provides flexibility for the lead to adjust during movement of the heart.

The lead body also has an intermediate section 30 which is proximal to the ventricular section for positioning intermediate the junction between the patient's atrium 28 and ventricle. The intermediate section begins at a point on the lead located from about 120 mm to about 170 mm from the distal end of the lead and extends to the beginning of the ventricular section of the lead. The intermediate section has a second pre-stressed portion with a second radius of curvature $R_2$. The second radius of curvature is suitably between about 20 mm and 30 mm. The second pre-stressed portion also provides flexibility for the lead to adjust during movement of the heart.

The lead body also has an atrial section 26 which is proximal to the intermediate section for positioning in the patient's atrium. The atrial section begins at a point on the lead located from about 150 mm to about 200 mm from the distal end of the lead and extends to the beginning of the intermediate section of the lead. The atrial section has a third pre-stressed portion with a third radius of curvature $R_3$. The third radius of curvature is suitably between about 20 mm and 30 mm. The third pre-stressed portion also provides flexibility for the lead to adjust during movement of the heart.

The ventricular, intermediate and atrial sections are constructed of flexible materials so as to have sufficient flexibility so that the atrial section is maintained in proximity to the patient's atrial wall during heart contractions or other heart movements. The ventricular section, however, may be relatively more stiff than either the intermediate or atrial sections of the lead in order to provide support for these two sections. The ventricular section may be made more stiff by several methods. For example, the ventricular section may be made thicker than the rest of the lead. An increase from 2.0 mm to about 2.5 mm in the diameter of the lead makes this section almost twice as stiff. Alternately, the portion of the ventricular section which is to be made more stiff may be made of a more stiffer material, such as, for example, polyurethane instead of silicone rubber. In addition, embodiments of the present invention which comprise a defibrillation coil of approximately 50 mm in length and 2.8 mm in diameter on the ventricular section make the ventricular section of the lead more stiff. Alternately, ad additional silicone rubber tubing can be placed over the ventricular section in order to make the ventricular section more stiff.

Still referring to FIG. 1, a preferred DDD pacing lead has at least one atrial electrode 18 positioned within the atrial section. The electrode is made of conductive materials well known those skilled in the art of leads. Preferably, the electrode is made of platina. Preferably, the electrode is a ring electrode with a diameter between about 2.0 to 5.0 mm, more preferably between about 3.0 to 3.5 mm. Preferably, the width of the ring electrode is between about 2.0 to 5.0 mm, more preferably between about 3.0 to 4.0 mm. Preferably, the ring electrode has a surface area of approximately 16 mm$^2$. The atrial rings may extend radially out from the lead body such that their circumference is slightly greater than the circumference of the lead body. An atrial conductor 22 within a lumen in the lead body connects the proximal end of the lead to the atrial electrode. In preferred embodiments of the invention, the lead has at least two atrial ring electrodes at about the center of the third radius of curvature. Of course, an embodiment of the invention contemplates a unipolar arrangement, using just one atrial electrode, and using the pacemaker as the other reference electrode.

Still referring to FIG. 1, a preferred DDD pacing lead further has at least one ventricular electrode 20 positioned within the ventricular section of the lead. The ventricular electrode may be a standard tip electrode known to those skilled in the art of leads or may be a ring electrode as described above. Preferably, the ventricular electrode is positioned at about the distal end of the lead. A ventricular conductor 24 within a lumen in the lead body connects the proximal end of the lead to the ventricular electrode. In preferred embodiments of the invention, the lead has two electrodes, e.g., one tip electrode and one ring electrode, or two ring electrodes. Of course, an embodiment of the invention contemplates a unipolar arrangement, using just one ventricular electrode, and using the pacemaker as the other reference electrode.

In another embodiment of the present invention, the DDD pacing lead may be used in connection with tachycardia conditions, in addition to bradycardia conditions. Still referring to FIG. 1, the ventricular section of the DDD pacing lead may optionally comprise a ventricular defibrillation coil 52 connected to the ventricular ring electrode. The defibrillation coil is preferably between 3 and 10 cm long, most preferably 5 cm long. The defibrillation coil is preferably between about 2.5 and 3.0 mm in diameter, more preferably about 2.8 mm in diameter. The defibrillation coil is able to deliver a shock of about 34 joules. The tachycardia DDD lead is preferably connected to an implantable pacing cardioverter defibrillator, or any other type of arrhythmia management device known to those skilled in the art.

Figure 2A:
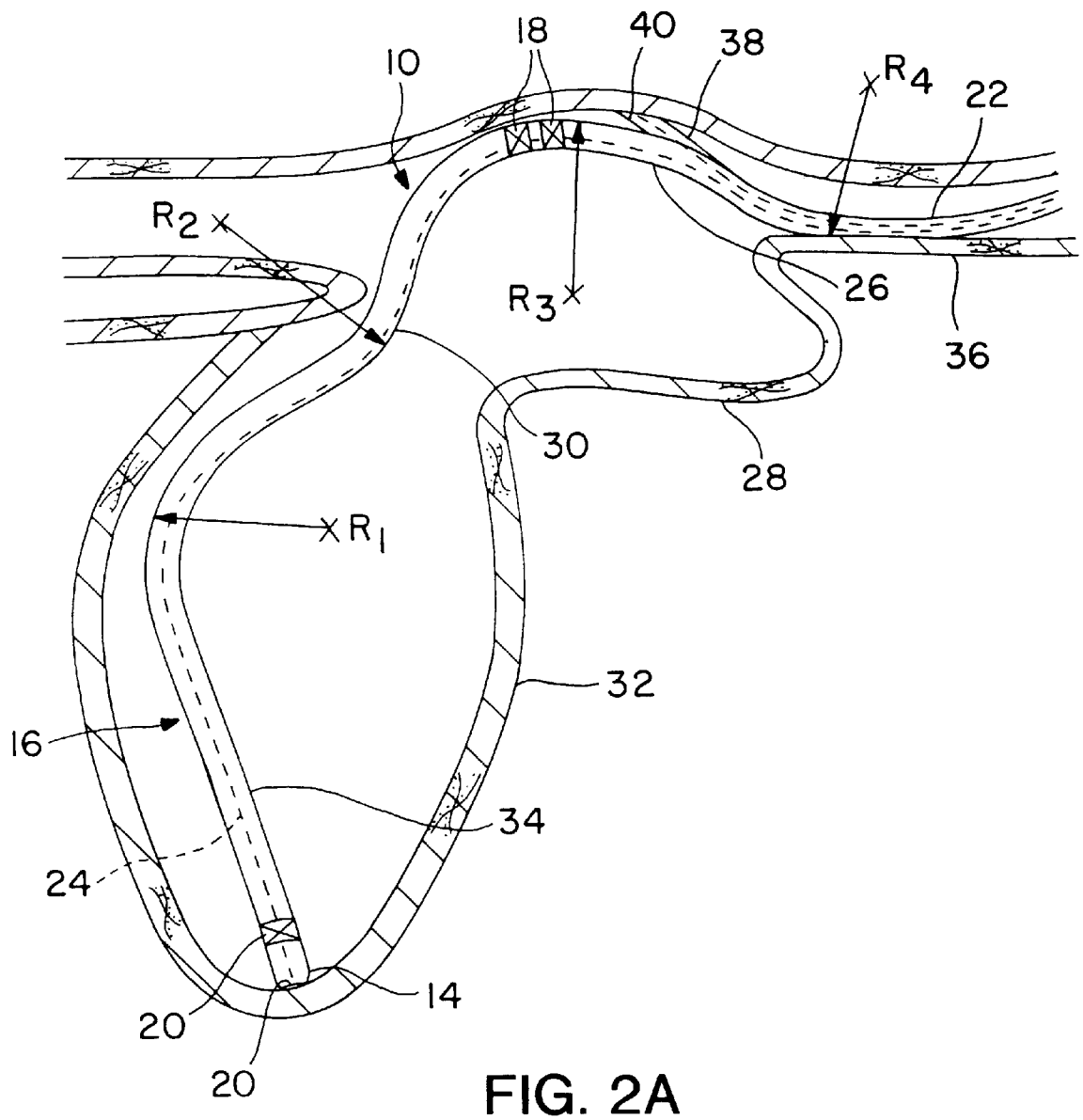
FIG. 2A is an illustrative representation of another preferred DDD pacing lead having a fourth radius of curvature and positioned within a patient's heart.

Referring now to FIG. 2A, shown is another preferred embodiment of the present invention in which the DDD pacing lead depicted in FIG. 1 also has a fourth pre-stressed portion which is proximal to the atrial section. The fourth pre-stressed portion is present in the portion of the lead which is positioned within the superior vena cava (SVC) 36. The fourth pre-stressed portion has a fourth radius of curvature $R_4$. Preferably, the fourth radius of curvature is between about 25 mm and 35 mm. The fourth pre-stressed portion also provides flexibility for the lead to adjust during movement of the heart. The fourth pre-stressed portion is preferably made of a material, such as, for example, silicon rubber, which provides structural integrity of the lead but yet provides flexibility.

Still referring to FIG. 2A, a preferred lead may also have a flexible lead extension 38 which is positioned adjacent to the third radius of curvature. Preferably, the flexible lead extension is proximal to the third radius of curvature. The flexible lead extension, however, may be positioned distal to the third radius of curvature. As shown in FIG. 2A, the flexible lead extension points toward the distal end of the lead. The flexible lead extension, however, may point towards the proximal end of the lead. The flexible lead extension serves as a tine so as to facilitate positioning of the lead against the atrial wall of the patient's heart. The flexible lead extension is preferably made of a non-conductive material well known to those skilled in the art of leads. In some embodiments of the invention, the flexible lead extension has an electrode 40 at its distal tip which serves as an atrial electrode. The electrode within the flexible lead extension may be either a tip electrode or a ring electrode. In embodiments where the flexible lead extension has an electrode, the electrode is further connected to the atrial conductor. In preferred embodiments of the invention, the lead has at least two atrial electrode rings and a flexible lead extension, with or without an additional atrial electrode, positioned adjacent to the third radius of curvature. In some embodiments of the invention, the pacing lead has at least one atrial electrode positioned in the portion of the lead that is positioned in the SVC when the ventricular section of the lead is positioned at the ventricular apex of the patient's heart.

Figure 2B:
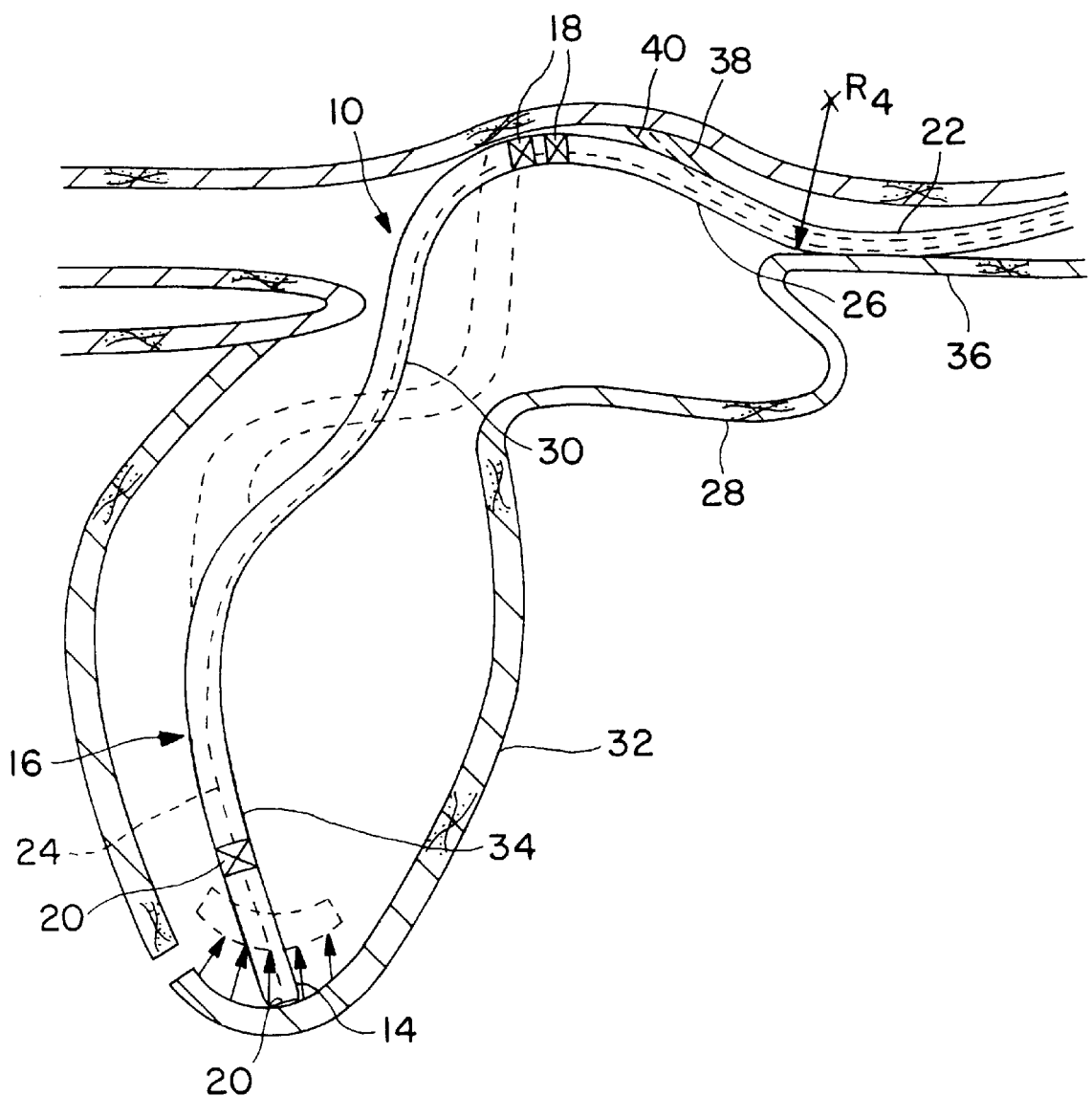
FIG. 2B is an illustrative representation of the pacing lead shown in FIG. 2A positioned within a patient's heart showing the movement of the lead upon contraction of the heart.

Referring now to FIG. 2B, shown is the DDD pacing lead depicted in FIG. 2A in a patient's heart which is contracting. As the patient's heart contracts, the apex of the ventricle moves in an upward direction (see the dotted lines showing the position of the apex of the ventricle during peak contraction). In animal studies, it has been observed that during ventricular contraction of the animal's heart, the pacing lead pushed up in a manner similar to that which is shown in FIG. 2B, which resulted in the atrial section of the lead being pressed against the atrial wall. Accordingly, in order to provide sufficient support and force to the atrial section of the lead, the ventricular section is preferably stiffer than the intermediate and atrial sections of the lead. In a typical contraction, the apex of the ventricle moves about 3 cm. The pre-stressed portions of the lead allow the lead to be flexible and thus accommodate the shape of the contracted heart while maintaining contact at the appropriate positions of the lead, e.g., where the electrodes are positioned. The fourth pre-stressed portion present in the portion of the lead, which is positioned in the SVC, maintains positioning of the atrial section of the lead at the appropriate site.

The leads of the present invention can be positioned in the patient's heart by using introducer sheaths or stylets, which are well known to those skilled in the art of leads. In addition, an anchoring sleeve may be used to fix the lead near its proximal end to a rib or some element in the pocket in order to prevent shifting of the pacemaker in a pocket from affecting the lead position in the heart. In addition, an advantage of using a lead without any atrial tines is that the practitioner can insert the lead into the heart using a smaller diameter introducer. Another advantage of Applicant's pacing lead is that when the ventricular section of the lead is positioned using a stylet and the stylet is removed, the atrial section of the lead is automatically positioned. Thus, there is no need to further position the atrial section, which saves implant time. The atrial section is also less dependent on anchoring sleeve fixation due to its flexible shape.

Referring now to FIG. 3, shown is a diagrammatic sketch of a pacing system in accordance with this invention. Pacemaker 50 is a standard DDD-type pacemaker, meaning that it has two pulse channels for delivering pacing pulses to the atrium and ventricle respectively. The pacemaker also has sensing channels for sensing and processing spontaneous signals from the atrium (via P waves) and ventricle (via R waves and T waves). The pacemaker may, of course, be a variation of a DDD-type, e.g., a DDD(R), or it can be a 4 chamber pacemaker which also has channels for pacing the left atrium and the left ventricle. As shown, pacemaker 50 is connected to the patient's heart by means of a lead 10, which is one of the above-described embodiments. Atrial electrodes 18 provide delivery of pace pulses to the atrium, and sense spontaneous P waves. Ventricular electrodes 20 provide delivery of pace pulses to the ventricle and sense R waves for transmission back to the pacemaker. Of course, a unipolar configuration could also be used in either or both chambers of the heart, in which case only one electrode would be necessary per chamber, the pacemaker being used as the other electrode.

What is claimed is:

1. An implantable pacing lead for DDD pacing of a patient's heart, said lead comprising:

a proximal end and a distal end, and a lead body extending therebetween;

said lead body comprising:

a ventricular section extending to said distal end for positioning in the patient's ventricle and having a first pre-stressed portion with a first radius of curvature;

an intermediate section proximal to said ventricular section for positioning intermediate the patient's atrium and ventricle and having a second pre-stressed portion with a second radius of curvature; and an atrial section proximal to said intermediate section for positioning in the patient's atrium and having a third pre-stressed portion with a third radius of curvature;

said ventricular, intermediate and atrial sections having flexibility sufficient so that said atrial section is maintained in proximity to the patient's atrial wall during heart contractions;

at least one atrial electrode positioned within said atrial section and an atrial conductor within said body connecting said proximal end to said atrial electrode; and at least one ventricular electrode positioned within said ventricular section at about said distal end and a ventricular conductor within said body connecting said proximal end to said ventricular electrode;

wherein said ventricular section begins at a point on said lead located from about 90 mm to about 150 mm from said distal end of said lead and extends to said distal end of said lead, said intermediate section begins at a point on said lead located from about 120 mm to about 170 mm from said distal end of said lead and extends to said beginning of said ventricular section, and said atrial section begins at a point on said lead located from about 150 mm to about 200 mm from said distal end of said lead aid extends to said beginning of said intermediate section.

2. The lead as described in claim 1 wherein said first radius of curvature is between about 25 mm and 35 mm, said second radius of curvature is between about 20 mm and 30 mm, and said third radius of curvature is between about 20 mm and 30 mm.

3. The lead as described in claim 1 further comprising a fourth pre-stressed portion proximal to said atrial section and having a fourth radius of curvature.

4. The lead as described in claim 3 wherein said fourth radius of curvature is between about 25 mm and 35 mm.

5. The lead as described in claim 1 wherein said lead comprises at least two atrial electrode rings at about the center of the third radius of curvature.

6. The lead as described in claim 1 further comprising a flexible lead extension positioned adjacent to said third radius of curvature.

7. The lead as described in claim 6 wherein said flexible lead extension comprises an electrode at its distal tip.

8. The lead as described in claim 1 further comprising at least two atrial electrode rings and a flexible lead extension positioned adjacent to said third radius of curvature.

9. The lead as described in claim 1 further comprising a ventricular defibrillation coil connected to said ventricular electrode.

10. A system for pacing a patient's heart, comprising:

a pacemaker; and a lead connectable therewith comprising:

a proximal end and a distal end, and a lead body extending therebetween;

said lead body comprising:

a ventricular section extending to said distal end for positioning in the patient's ventricle and having a first pre-stressed portion with a first radius of curvature;

an intermediate section proximal to said ventricular section for positioning intermediate the patient's atrium and ventricle and having a second pre-stressed portion with a second radius of curvature; and an atrial section proximal to said intermediate section for positioning in the patient's atrium and having a third pre-stressed portion with a third radius of curvature;

said ventricular, intermediate and atrial sections having flexibility sufficient so that said atrial section is maintained in proximity to the patient's atrial wall during heart contractions;

at least one atrial electrode positioned within said atrial section and an atrial conductor within said body connecting said proximal end to said atrial electrode; and at least one ventricular electrode positioned within said ventricular section at about said distal end and a ventricular conductor within said body connecting said proximal end to said ventricular electrode;

wherein said ventricular section begins at a point on said lead located from about 90 mm to about 150 mm from said distal end of said lead and extends to said distal end of said lead, said intermediate section begins at a point on said lead located from about 120 mm to about 170 mm from said distal end of said lead and extends to said beginning of said ventricular section, and said atrial section begins at a point on said lead located from about 150 mm to about 200 mm from said distal end of said lead and extends to said beginning of said intermediate section.

11. The system as described in claim 10 wherein said first radius of curvature is between about 25 mm and 35 mm, said second radius of curvature is between about 20 mm and 30 mm, and said third radius of curvature is between about 20 mm and 30 mm.

12. The system as described in claim 10 further comprising a fourth pre-stressed portion proximal to said atrial section and having a fourth radius of curvature.

13. The system as described in claim 12 wherein said fourth radius of curvature is between about 25 mm and 35 mm.

14. The system as described in claim 10 wherein said lead comprises at least two atrial electrode rings at about the center of the third radius of curvature.

15. The system as described in claim 10 further comprising a flexible lead extension positioned adjacent to said third radius of curvature.

16. The system as described in claim 15 wherein said flexible lead extension comprises an electrode at its distal tip.

17. The system as described in claim 10 further comprising at least two atrial electrode rings and a flexible lead extension positioned adjacent to said third radius of curvature.

* * * * *